United States Patent
Blum

(10) Patent No.: US 10,138,173 B1
(45) Date of Patent: Nov. 27, 2018

(54) ZONE REFINING METHOD FOR NUTRACEUTICALS

(71) Applicant: White Flower Associates, Lindenhurst, NY (US)

(72) Inventor: Mel Blum, Wantagh, NY (US)

(73) Assignee: White Flower Associates, Lindenhurst, NY (US)

( * ) Notice: Subject to any disclaimer, the term of this patent is extended or adjusted under 35 U.S.C. 154(b) by 0 days.

(21) Appl. No.: 15/730,274

(22) Filed: Oct. 11, 2017

(51) Int. Cl.
| | |
|---|---|
| *C03B 33/00* | (2006.01) |
| *C07B 63/00* | (2006.01) |
| *C30B 33/00* | (2006.01) |
| *A61K 36/00* | (2006.01) |
| *B01J 23/72* | (2006.01) |
| *B01J 23/75* | (2006.01) |
| *B01J 23/648* | (2006.01) |

(52) U.S. Cl.
CPC ............ *C07B 63/00* (2013.01); *A61K 36/00* (2013.01); *B01J 23/6482* (2013.01); *B01J 23/72* (2013.01); *B01J 23/75* (2013.01); *C30B 33/00* (2013.01)

(58) Field of Classification Search
CPC ......... C30B 33/00; C30B 23/72; C30B 23/75; B01J 23/72; B01J 23/75
See application file for complete search history.

(56) References Cited

U.S. PATENT DOCUMENTS 6,946,406 B2 * 9/2005 Yamazaki ............... B05D 1/60
438/780

FOREIGN PATENT DOCUMENTS

| | | |
|---|---|---|
| CN | 1667049 A | 9/2005 |
| CN | 103664934 A | 3/2014 |
| EP | 2329815 A1 | 6/2011 |

OTHER PUBLICATIONS

William R Wilcox, et al., "Zone Melting of Organic Compounds", School of Pharmacy, Sate University of New York at Buffalo, Buffalo, New York, Jan. 16, 1964, pp. 187-220.

* cited by examiner

*Primary Examiner* — Robert M Kunemund
(74) *Attorney, Agent, or Firm* — Norris McLaughlin, P.A.

(57) ABSTRACT

Disclosed is a method for purifying an organic compound, comprising the steps of (i) providing a crystalline sample of organic compound having a first impurity level, (ii) adding a catalyst to the sample, (iii) heating a portion of the sample to a temperature at or above melting point of the organic compound so as to create a molten zone of the sample, (iv) moving application of heat down the length of the sample, such that the molten zone is moved along the length of the sample, (v) collecting molten material at an end of the sample, (vi) optionally grinding the sample back to a powder, (vii) repeating steps (i)-(iv) at least two more times, and (viii) obtaining a purified sample having a second impurity level, which is lower than the first impurity level, wherein the organic compound is a nutraceutical selected from the group consisting of vinpocetine, huperzine, astragalosides, HEPPS buffer, curcumin, piperine, uridine, capsaicin and kinetin.

17 Claims, 1 Drawing Sheet

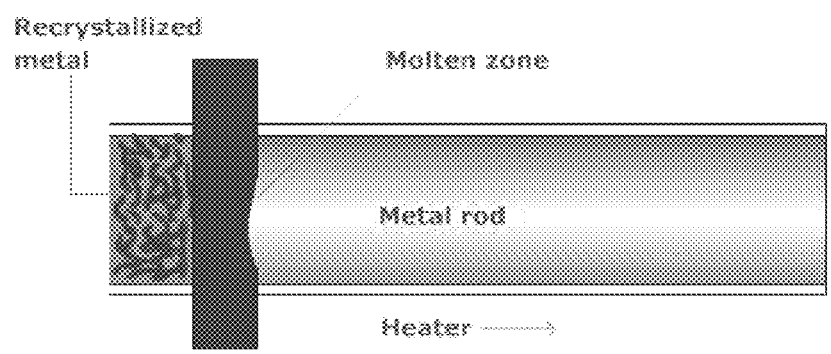
--PRIOR ART--

ZONE REFINING METHOD FOR NUTRACEUTICALS

FIELD OF THE INVENTION

The present invention is generally concerned with a zone refining method to purify certain organic compounds known as "nutraceuticals", which method utilizes catalysts to achieve high resulting purity.

DISCUSSION AND COMPARISON WITH RELEVANT PRIOR ART

Zone refining or "zone melting" is a group of similar methods for purifying a material (e.g., crystals, chemicals, and metals) in which a narrow region of the material is melted, and this molten zone is moved along the material. The molten region melts impure solid at its forward edge and leaves a wake of purer material solidified behind it as it moves through the ingot or batch (see e.g., FIG. 1). The impurities concentrate in the melt, and move to one end of the ingot or batch of the material.

Zone refining was first developed as a method to prepare high purity semiconductor materials. Wilcox et al. "Zone Melting of Organic Compounds", pages 187-220, published April 1964 (hereinafter "Wilcox") describe application of zone melting techniques to purify organic compounds, the disclosure of which publication is incorporated herein by reference. According to Wilcox, an important advantage of the zone melting process is that there is no contact between the compound being purified and any other solvent or chemical.

Although the term "nutraceuticals" does not exist as a regulatory category in the United States, it is widely used in the marketplace to refer to a pharmaceutical-grade and standardized nutrient. In the U.S., the Food and Drug Administration (FDA) regulates these "nutraceuticals" as dietary supplements and food additives. Examples of such "nutraceuticals" include vinpocetine, huperzine, astragalosides, HEPPS buffer, curcumin, piperine, uridine, capsaicin and kinetin.

According to Chinese Publication No. CN1667049A, curcumin has known medical applications. However, because curcumin is a relatively insoluble organic compound, it can be difficult to include in pharmaceutical formulations such as injectables. As a solution, CN'049 proposes a method for preparing soluble curcumin comprising two main steps, the first being refinery of curcumin, and the second being making the curcumin of step one soluble. Step two of CN'049 comprises adding the refined curcumin from step one to a solution comprising a metal salt (e.g., copper chloride, calcium chloride or zinc chloride) to obtain soluble curcumin. According to CN'049, addition of metal ions in step two allows the curcumin to become soluble without affecting its pharmaceutical properties. However, CN'049 does not teach zone refining.

Chinese Publication No. CN103664934A describes a method for preparing vinpocetine, the method comprising the following steps: reacting raw material (vincamine) with esterifying agents (triethyl orthoformate, triethyl orthoacetate or triethyl orthoproprionate) under the effect of a Lewis acid (e.g., cuprous chloride, copper complex etc.), obtaining the crude product, washing the obtained crude product by alkaline solution, decolorizing by alcohol, and recrystallizing. Notably, CN'934 does not teaching using said Lewis acid to catalyze a reaction with vinpocetine.

Finally, European Publication No. EP2329815A1 teaches that *Capsicum* species are an important source of a variety of carotenoids, with zeaxanthin being the dominant carotenoid found in dried ripe fruit pod flesh, when measured in non-esterified forms. The teaching of EP'815 is concerned with *Capsicum* plants producing greater than about 0.4% zeaxanthin, by weight in the dried, ripe fruit pod flesh. EP'815 further provides a plant extract composition comprising zeaxanthin derived from the *Capsicum* plant, which may further comprises a long list of additional components (para. [0074]), which list includes curcumin. EP'815 mentions the term "zone refining" in two separate instances. Paras. [0128] and [0130] of EP'815 teach that the plant product comprising zeaxanthin and extracts of *Capsicum* plant flesh according to the disclosure therein can be further processed by suitable techniques, and provides a long, non-exclusive list of such suitable techniques, which list includes zone refining. Notably, there is no teaching to apply the zone refining technique to curcumin.

In this application, a new zone refining method is provided utilizing certain metal salts (e.g., oxides, oxychlorides and chlorides of copper, vanadium, and cobalt) as catalysts for obtaining high purity "nutraceuticals". None of foregoing Wilcox, CN'049, CN'934 or EP'813 teaches using these catalysts in a zone refining process to purify nutraceuticals. Moreover, Wilcox in fact states that "[t]he outstanding advantage of the zone melting procedure is that there is no contact between the compound being purified and any other solvent or chemical", making use of a "foreign" catalyst according to the present invention even more unobvious.

Prior to the inventive method as described herein, known techniques for purifying organic chemicals can either only reach limited purities and/or be prohibitively expensive. Conventional purification techniques include recrystallization which can only reach purities of, at best, up to 90%. Ion exchange may produce organic chemicals with purities of 99.9% or 99.95%, but at a very high cost. The present invention represents an improvement from the prior art by providing a cost-effective way to obtain organic chemicals having a higher purity than could be achieved previously. Such high purities are especially important for nutraceuticals as they are intended for human consumption.

These and further aspects of the invention will be understood with reference to the following specification and drawing(s).

SUMMARY OF THE INVENTION

Disclosed is a method for purifying an organic compound, comprising the steps of (i) providing a crystalline sample of organic compound having a first impurity level, (ii) adding a catalyst to the sample, (iii) heating a portion of the sample to a temperature at or above melting point of the organic compound so as to create a molten zone of the sample, (iv) moving application of heat down the length of the sample, such that the molten zone is moved along the length of the sample, (v) collecting molten material at an end of the sample, (vi) optionally grinding the sample back to a powder, (vii) repeating steps (i)-(iv) at least two more times, and (viii) obtaining a purified sample having a second impurity level, which is lower than the first impurity level, wherein the organic compound is a nutraceutical selected from the group consisting of vinpocetine, huperzine, astragalosides, HEPPS buffer, curcumin, piperine, uridine, capsaicin and kinetin.

BRIEF DESCRIPTION OF THE DRAWINGS

FIG. 1: illustrates a prior art zone melting technique to purify a metal rod.

DETAILED DESCRIPTION

This invention provides a method for purifying an organic compound, comprising the steps of (i) providing a crystalline sample of organic compound having a first impurity level, (ii) adding a catalyst to the sample, (iii) heating a portion of the sample to a temperature at or above melting point of the organic compound so as to create a molten zone of the sample, (iv) moving application of heat down the length of the sample, such that the molten zone is moved along the length of the sample, (v) collecting molten material at an end of the sample, (vi) optionally grinding the sample back to a powder, (vii) repeating steps (i)-(iv) at least two more times, and (viii) obtaining a purified sample having a second impurity level, which is lower than the first impurity level, wherein the organic compound is a nutraceutical selected from the group consisting of vinpocetine, huperzine, astragalosides, HEPPS buffer, curcumin, piperine, uridine, capsaicin and kinetin.

In one embodiment of the method described herein, the catalyst is an oxide, oxychloride or chloride of copper, vanadium, or cobalt, or a mixture thereof. In another embodiment, the catalyst is copper oxychloride, cuprous choride, cupric chloride, or a mixture thereof.

In one embodiment, the concentration of catalyst used is about 5-100 ppm. In another embodiment, the concentration of catalyst used is about 5-10 ppm. In yet another embodiment, the concentration of catalyst used is about 10 ppm.

In one embodiment, the catalyst is a fine powder having a particle size of about 10 microns or less. In another embodiment, catalyst has a particle size of less than about 10 microns.

In one embodiment, steps (i)-(iv) are repeated at least four times. In another embodiment, steps (i)-(vi) are repeated at least twice. In yet another embodiment, steps (i)-(vi) are repeated at four times.

In one embodiment, the method further comprises a step of analyzing the sample to determine purity level of the sample.

In one embodiment, steps (i), (ii) and/or (iii) are performed at a temperature of at least 100° C. In another embodiment, steps (i), (ii) and/or (iii) are performed at a temperature of about 200° C. or above.

In one embodiment, movement of heat application in step (iv) is vertical. In another embodiment, movement of heat application in step (iv) is horizontal.

Finally, also provided is a purified sample of organic compound obtained by the various embodiments of the method as described herein.

Terms

As used herein, and unless stated otherwise, each of the following terms shall have the definition set forth below.

As used herein, "about" in the context of a numerical value or range means±10% of the numerical value or range recited or claimed. By any range disclosed herein, it is meant that all hundredth, tenth and integer unit amounts within the range are specifically disclosed as part of the invention. Accordingly, "about" a recited value specifically includes that recited value. For example, about 10 ppm refers to all sizes within the range of ±10% of 10 ppm including 10 ppm.

As used herein, the term "nutraceutical" refers to any high purity, standardized grade of fortified or concentrated food substance, herbal, vitamin, mineral, amino acid, ayurvedic or dietary supplement which when administered can or have been known to provide health or medical benefits in addition to its basic nutritional value. Examples of nutraceuticals in accordance with the inventive method described herein include but are not limited to vinpocetine, huperzine, astragalosides, HEPPS buffer, curcumin, piperine, uridine, capsaicin and kinetin.

An embodiment of the disclosed method comprises.
  (i) providing a (optionally solid and/or powder) crystalline sample of nutraceutical having a first (e.g., standard) impurity level,
  (ii) adding a catalyst, optionally selected from the group consisting of an oxide, oxychloride or chloride of copper, vanadium, or cobalt, or a mixture thereof, wherein the catalyst preferably having cations with valences of the "-ous" or "-ic" suffix.
  (iii) heating a portion of the sample to a temperature at or above the melting point of the nutraceutical so as to create a molten zone of the sample,
  (iv) moving application of heat down the (preferably full) length of the sample, such that the molten zone is moved along the (preferably full) length of the sample,
  (v) collecting molten material at an end of the sample and optionally analyzing the sample to determine purity level of the sample,
  (vi) optionally grinding the sample back to a powder and optionally analyzing the sample to determine purity level of the sample,
  (vii) repeating steps (i)-(iv) at least two more times (passes), or repeating steps (i)-(v) at least two more times (passes), or repeating steps (i)-(vi) at least two more times (passes), and
  (viii) obtaining a purified sample having a second impurity level, which is lower than the first impurity level, and optionally analyzing the sample to determine purity level of the sample.

In an embodiment of the inventive method as described herein, the sample is analyzed to determine purity level of the sample after each pass, after every 2 passes, or after every 3 passes, etc. Appropriate analytical methods are known to those having ordinary skill in the art. Examples of such analytical methods include, but are not limited to, high-performance liquid chromatography (HPLC), mass spectrometry (MS), thin-layer chromatography (TLC), and nuclear magnetic resonance spectroscopy, most commonly known as NMR spectroscopy.

Finally, the combination of any embodiment or feature mentioned herein with one or more of any of the other separately mentioned embodiments or features is contemplated to be within the scope of the instant invention.

EXPERIMENTS

The below described series of experiments were conducted using the Instrolec 300 Zone Refiner, which was a vertical research and development (R&D) unit capable of reaching temperatures of up to 300° C. Nutraceuticals were zone refined in accordance with method steps substantially as that described hereinabove, catalyzed with the following catalysts at levels of 5-10 ppm: copper oxychloride, cuprous chloride or cupric chloride.

The Instrolec 300 Zone Refiner was originally produced in the United Kingdom but is no longer available. However, similar results are expected by using other commercial low temperature zone refiners for organic chemicals, such as the MiniZone™ zone refiner available from Design Scientific (Holland, Mich.), modified by attaching a radio frequency (RF) induction heating system to increase temperature capabilities. An appropriate cooling system should also be attached because too high a temperature will tend to decompose the containers for the organic chemicals. Additional zone refiners for organic chemicals such as that made by SMART Laboratories of Kansas State University (KSU), by Bhabha Atomic Research Centre (BARC) of Mumbai, India, by State Research and Design Institute of the Rare Metal Industry (GIREDMET) of Russia, or the flat bed/horizontal unit described in U.S. Pat. No. 6,030,588, are expected to be similarly useful by modifying the low temperature unit to increase the maximum temperature reachable from 200° C. to 300° C. or higher.

Experiment 1: Zone Refining of Nutraceuticals Using Instrolec 300 Zone Refiner

Results from the first set of runs are shown in Table 1 below.

ride or zirconium oxychloride were used instead, the zone refining did not work or did not work as well (e.g., the nutraceuticals either decomposed or was not purified, or was purified to a level which is below an acceptable or desirable level).

Experiment 4: Comparative Testing to Vary Catalyst Amount

Additional runs were performed wherein the catalyst particle size in each case exceeds 10 μm. Specifically, catalysts with particle sizes ranging from 30-50 μm were used. When particle sizes of the catalyst used exceed 10 μm, the zone refining did not work or did not work as well (e.g., the nutraceuticals either decomposed or was not purified, or was purified to a level which is below an acceptable or desirable level). When the catalysts were air milled down to 1-10 μm, the zone refining worked better in comparison.

Experiments 1-4: Discussion

Experiments 1-4 and Table 1 demonstrate that catalysts are required for the zone purification process to work or work well. Further, the inventor has determined that cata-

TABLE 1

Zone refining of nutraceuticals using Introlec 300 Zone Refiner

| | Nutraceutical | MP (° C.) | Starting purity (%) | Catalyst | Catalyst level (ppm) | Catalyst particle size (μm) | Passes | Process Temp (° C.) | Ending catalyst level (ppm) | Ending Nutraceutical purity (%) |
|---|---|---|---|---|---|---|---|---|---|---|
| Inventive Ex.1 | Vinpocetine | 149 | 95 | CuOCl | 10 | 1-10 | 3 | 200 | 0.36 | 99.995+ |
| Inventive Ex. 2 | Huperzine | 213 | 93 | CuOCl | 10 | 1-10 | 3 | 250 | 0.5 | 99.995+ |
| Inventive Ex. 3 | Astragaloside IV | 290 | 97 | CuOCl | 10 | 1-10 | 2 | 300 | 0.58 | 99.98+ |
| Inventive Ex.4 | HEPPS Buffer | 237 | 99 | CuOCl | 10 | 1-10 | 3 | 275 | 0.28 | 99.999+ |
| Inventive Ex. 5 | Curcumin | 184 | 95 | $CuCl_2$ | 10 | 1-10 | 3 | 250 | 0.44 | 99.995+ |
| Inventive Ex.6 | Piperine | 130 | 97 | CuOCl | 10 | 1-10 | 3 | 200 | 0.35 | 99.998+ |
| Inventive Ex.7 | Uridine | 167 | 99 | CuOCl | 10 | 1-10 | 3 | 200 | 0.45 | 99.999+ |
| Inventive Ex. 8 | Kinetin | 270 | 98 | $CuCl_2$ | 10 | 1-10 | 2 | 300 | 4.1 | 99.97+ (also sublimes) |
| Inventive Ex.9* | Capsaicin | 65 | 98 | CuOCl | 10 | 1-10 | 1 | 200 | 2.2 | 99.97 |

*For Inventive Example 9, the zone refiner collapsed after the first pass. The starting purity was ~98%. Only one pass of the zone refiner resulted in a purity of 99.97%. The inventors expect that purities of 99.995-99.999% would have been possible with additional passes.

Experiment 2: Comparative Testing without Catalysts

Additional runs were performed where catalysts were not used. Without catalysts, vinpocetine was purified from ~95% to 97%, huperzine was purified from 93% to 96%, astragaloside IV and capsaicin stayed at the same purity (no purification), and kinetin decomposed. Accordingly, when catalysts were not used, the zone refining did not work or did not work as well (e.g., the nutraceuticals either decomposed or was not purified, or was purified to a level which is below an acceptable or desirable level).

Experiment 3: Comparative Testing with Additional Catalysts

Additional runs were performed using different catalysts, including copper, vanadium and cobalt along with their oxides, oxychlorides and chlorides. When manganese chlolysts with particle sizes below 10 microns work best. The catalysts are ultimately zone refined out to levels of 0.1-0.5 ppm's. Most nutraceuticals according to Table 1 below were zone refined to purities ranging from 99.995+% to 99.999+%.

In sum, the inventor surprisingly found that zone refining of nutraceuticals catalyzed with certain catalysts enables one to obtain nutraceuticals of very high purity levels. The high purity nutraceuticals are useful as analytical standards, or as high purity premium starting materials.

Experiment 5: Comparative Testing to Vary Catalyst Level (ppm)

Additional runs can be performed to vary catalyst level. It is expected that when the catalyst level exceeds 100 ppm, the catalyst themselves would likely break down during the zone refining process causing the run to fail. 10-100 ppm is being considered the acceptable catalyst level to be used in the inventive methods described herein.

What is claimed is:

1. A method for purifying an organic compound, comprising the following steps:
   (i) providing a crystalline sample of organic compound having a first impurity level,
   (ii) adding a catalyst to the sample,
   (iii) heating a portion of the sample to a temperature at or above melting point of the organic compound so as to create a molten zone of the sample,
   (iv) moving application of heat down the length of the sample, such that the molten zone is moved along the length of the sample,
   (v) collecting molten material at an end of the sample,
   (vi) optionally grinding the sample back to a powder,
   (vii) repeating steps (i)-(iv) at least two more times, and
   (viii) obtaining a purified sample having a second impurity level, which is lower than the first impurity level,
   wherein the organic compound is a nutraceutical selected from the group consisting of vinpocetine, huperzine, astrazaloside IV, HEPPS buffer, curcumin, piperine, uridine, capsaicin and kinetin.

2. The method of claim 1, wherein the catalyst is an oxide, oxychloride or chloride of copper, vanadium, or cobalt, or a mixture thereof.

3. The method of claim 2, wherein the catalyst is copper oxychloride, cuprous choride, cupric chloride, or a mixture thereof.

4. The method of claim 1, wherein the concentration of catalyst used is about 5-100 ppm.

5. The method of claim 4, wherein the concentration of catalyst used is about 5-10 ppm.

6. The method of claim 5, wherein the concentration of catalyst used is about 10 ppm.

7. The method of claim 1, wherein the catalyst is a fine powder having a particle size of about 10 microns or less.

8. The method of claim 7, wherein the catalyst has a particle size of less than about 10 microns.

9. The method of claim 1, wherein steps (i)-(iv) are repeated at least four times.

10. The method of claim 1, wherein steps (i)-(vi) are repeated at least twice.

11. The method of claim 10, wherein steps (i)-(vi) are repeated at four times.

12. The method of claim 1, further comprising a step of analyzing the sample to determine purity level of the sample.

13. The method of claim 1, wherein steps (i), (ii) and/or (iii) are performed at a temperature of at least 100° C.

14. The method of claim 13, wherein steps (i), (ii) and/or (iii) are performed at a temperature of about 200° C. or above.

15. The method of claim 1, wherein movement of heat application in step (iv) is vertical.

16. The method of claim 1, wherein movement of heat application in step (iv) is horizontal.

17. A purified sample of organic compound obtained by the method of claim 1.

* * * * *